United States Patent [19]

Updike et al.

[11] 4,240,438
[45] Dec. 23, 1980

[54] METHOD FOR MONITORING BLOOD GLUCOSE LEVELS AND ELEMENTS

[75] Inventors: Stuart J. Updike; Mark C. Shults, both of Madison, Wis.

[73] Assignee: Wisconsin Alumni Research Foundation, Madison, Wis.

[21] Appl. No.: 947,949

[22] Filed: Oct. 2, 1978

[51] Int. Cl.³ .................. A61B 5/00; G01N 27/26
[52] U.S. Cl. ..................... 128/635; 204/195 B
[58] Field of Search ........... 128/635, 768; 204/195, 204/290 R, 290 F

[56] References Cited

U.S. PATENT DOCUMENTS

| | | | |
|---|---|---|---|
| 3,838,682 | 10/1974 | Clark et al. | 128/635 |
| 3,857,771 | 12/1974 | Sternberg | 204/195 B |

OTHER PUBLICATIONS

"The Immobilization of Enzymes on Nylon Structures and Their Use in Automated Analysis," Biochem J., Great Britain, Inman et al., 2-1972.
"Construction and Characteristics of Teflon Covered Electrode for IV Oxygen Determination," *The Review of Scientific Instruments*, Krog et al., vol. 30, No. 2, 11-1958.
"O₂ Tension Monotoring," *Med. Instrumentation*, Scacci et al., vol. 10, #4, 8-1976.

*Primary Examiner*—Robert W. Michell
*Assistant Examiner*—Thomas Wallen
*Attorney, Agent, or Firm*—McDougall, Hersh & Scott

[57] ABSTRACT

A method for monitoring blood glucose levels at frequent intervals, which includes a method for equalizing the temperature and oxygen level in the blood and sensing the rate of oxygen consumption by the glucose contained in the blood in the presence of glucose oxidase enzyme immobilized on a hydrophobic membrane covering a measurement electrode and elements employed therein including the equalizing method and the electrode and method for preparing same.

16 Claims, 4 Drawing Figures

METHOD FOR MONITORING BLOOD GLUCOSE LEVELS AND ELEMENTS

The invention described herein was made in the course of work under a grant or award from the Department of Health, Education, and Welfare.

This invention relates to a means and method for monitoring blood glucose levels and to elements employed in the practice of same.

Referring to diabetes, as illustrative of the need for rapid and frequent analysis of blood glucose levels, diabetes is characterized by elevated blood glucose. The severity of this disturbance, and the extent to which diet and insulin treatment are successful in maintaining blood glucose in the normal range is believed to determine onset and severity of the devastating renal, retinal and cardiovascular manifestations of the disease.

In diabetic patients dependent on insulin injections, total absence of endogenous insulin, antibody against insulin, or less understood types of "insulin resistance", control of glucose can be particularly difficult.

In these patients, checking for spill of glucose into the urine and spot blood glucose determinations on an outpatient basis may not provide sufficient information to bring blood glucose back under control. Thus hospitalization for more intense study is required.

Furthermore, determining glucose spill into the urine can sometimes lead to an erroneous judgment about the patient's current insulin requirement. This is because some diabetics spill glucose into the urine from the effects of too much, rather than too little, insulin. The cause of this seeming paradox is recurrent hypoglycenic insulin reactions. Each of these reactions is transient and may or may not cause symptoms, but is followed by a massive rebound hyperglycemia, mediated through adrenalin and glucagon release and less well understood mechanism. To evaluate and successfully treat these patients, the physician must obtain frequent blood glucose determinations.

Frequent blood glucose determination is also desirable when a diabetic patient is acutely ill, undergoing surgery, childbirth, or suffering from severe ketoacidosis. Occasionally, non-diabetic patients such as the acutely ill patient treated with a pharmacologic dose of corticosteroid, or the patient with recurrent fainting spells who is suspect of having functional hypoglycemia needs to have frequent serial blood glucose determinations made.

In summary, there is a need for an instrument, preferably a portable instrument, suitable for continuous glucose monitoring. Numerous attempts have been made to provide this capability but, to the present, no instrument has emerged which is sufficiently free from problems for acceptance into broad clinical use. Problems encountered have included poor precision of the glucose detector, clotting and drift in the blood sampling system, and non-linearity of the signal output. Such instruments tend to be complicated and have required frequent and sometimes complex calibration.

It is an object of this invention to provide an instrument and method for frequent and rapid analysis of blood glucose, which is relatively free of the problems heretofore encountered, which is portable to enable use for a bedside instrument for continuous monitoring of blood glucose levels in a patient, which can be automated for maintaining a predetermined analysis program, and which is relatively free of clotting and/or drift in the system for blood sampling and linear in the signal output, and it is a related object to produce and to provide elements for use in the successful operation of the blood glucose analyzer for monitoring blood glucose levels.

These and other objects of this invention will hereinafter appear and for purposes of illustration, but not of limitation, embodiments of the invention are shown in the accompanying drawings in which.

In accordance with the practice of this invention, use is made of a glucose detector embodying an immobilized enzyme electrode which can be operated in a rate detection mode. The high performance of the detector is based, in part, on the development of an electrode covered with a hydrophobic membrane, such as Teflon, having glucose oxidase bonded onto the surface thereof in an immobilized state.

The invention will be described with reference to an instrument, diagrammatically illustrated in FIG. 1, for analysis of blood glucose at frequent intervals for substantially continuous monitoring of glucose levels in patients' blood. While description will be made for operation over 2 minute intervals, it will be understood that the frequency of determinations for blood glucose levels can be made on more frequent or less frequent intervals, but on an intermittent basis, as will hereinafter be described.

Figure 1:
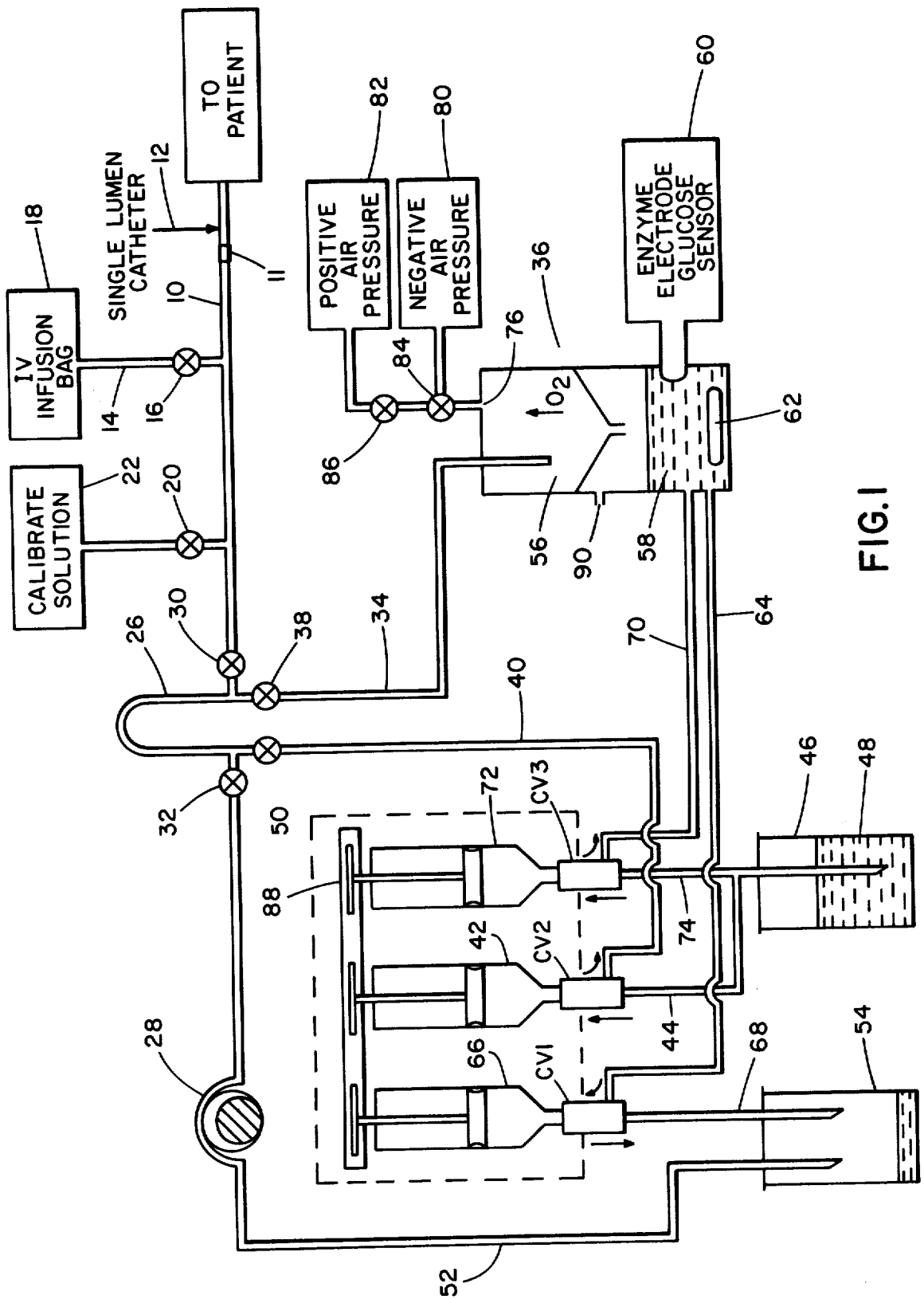
FIG. 1 is a flow diagram of a blood glucose analyzer embodying the features of this invention.

The instrument diagrammed in FIG. 1 comprises a small bore plastic tube 10 fitted with an intravenous single lumen luer lock 11 connected catheter 12. Connected to this tube via line 14, fitted with a pinch valve 16, is an intravenous infusion bag 18 adapted to be filled with a sterile pharmacological saline solution containing sufficient heparin, about 400µ per liter, for infusion to prevent any thrombus formation in the catheter between cycles for drawing patient's blood. Also connected to the tube 10 is a second line 20 leading to a container 22 adapted to be filled with a solution containing a calibrated amount of glucose for calibrating the instrument, the flow of which into the tubing system is controlled by a pinch valve 24.

A blood sample loop 26 of a measured volume is interposed in the line between a blood sample pump 28 and the catheter, preferably between the inlet from the source of calibrating solution and the pump, with pinch valves 30 and 32 on opposite sides of the loop for closing off the loop. One end of the blood sample loop 26 is connected by line 34 to the analyzer 36 with a pinch valve 38 to isolate the loop from the analyzer, while the other end of the loop is connected by line 40 to the outlet of a syringe 42. The inlet of the syringe communicates through line 44 to a source 46 of a buffer solution 48 such as a phosphate buffer, with pinch valve 50 in line 40 to isolate the blood sample loops from the syringe. Line 52 connects the outlet from the pump 28 to waste which may be in the form of a waste container 54.

In the illustrated modification, the analyzer 36 is formed with an upper compartment 56 for first bringing the blood sample to oxygen and temperature equilibrium before the sample is displaced from the upper compartment to a lower electrode sensing cuvette 58 containing the enzyme electrode glucose sensor 60, hereinafter to be described in greater detail, and a magnetic stirring bar 62 for rapid mixing of the sample during analysis.

The cuvette is provided with an outlet in the bottom portion which is connected by line 64 to the inlet of syringe 66 while the outlet from the syringe 66 is connected by line 68 to waste, such as container 54. The cuvette is also provided with an inlet connected by line 70 to the outlet from syringe 72 while the inlet to the syringe 72 is connected by line 74 to a source 48 of a buffer solution, such as a phosphate buffer. The cuvette is provided with an orifice 90 to maintain the cuvette at atmospheric pressure.

The upper compartment 56 has an outlet 76 in the upper portion connected by line 78 to a source of negative air pressure, indicated by the numeral 80, and to a source of positive air pressure, indicated by the numeral 82. The line 78 is provided with a valve 84 for controlling communication of the negative air pressure line and a valve 86 for controlling communication with the positive air pressure line.

The syringes 42, 66 and 72 are preferably joined in a syringe table 88 for conjoint actuation of the piston type actuator in each of the three syringes.

In operation, with valves 16, 24, 38 and 50 closed, and valves 30 and 32 open, the catheter 12 is connected into a blood vessel of the patient and the pump 28 is operated over a 20 second period for withdrawal of patient's blood into and through the sample loop 26 to fill the loop. In the illustrated modification, when use is made of a canula 10 having a diameter of 0.03 inch and a length of 3 feet, 200 microliters of blood is drawn over a 20 second interval to fill the sample loop 26 with the patient's blood. At the same time, the syringe table is raised to draw buffer into the syringes 42 and 72 and to empty the electrode cuvette by withdrawal of the contents thereof into the syringe 66.

During the remainder of the blood analysis cycle, and until the next cycle occurs, with valves 30 and 32 closed and valve 16 open, heparinized saline drains back through line 10 at a rate of ½ to 1 ml/minute to flush the catheter to prevent any thrombus formation in the catheter.

Meanwhile, with valves 38 and 50 open and valves 30, 32, and 86 closed and valve 84 switched to negative air pressure, the syringe table is operated to displace fluids from the syringes to (1) deliver waste from syringe 66 to the waste container 54, (2) deliver buffer from the syringe 72 through line 70 to the electrode cuvette 58, and (3) to flush the sample from the sample loop 26 through line 34 into the equilibration chamber 56. The blood sample trapped in the sample loop, in a measured amount of 40 microliters, is thus washed into the chamber 56 with 200 microliters of buffer, such as a 0.2 M phosphate buffer at pH 6.0.

After the blood sample has been delivered to the equilibration chamber 56, equilibration of the whole blood sample to 37° C. and the oxygen tension to that of ambient air is achieved by opening valve 84 to activate the negative air pressure system which draws room air which has been equilibrated to 36° C. upwardly through orifice 90 through a distributor at the base of chamber 56 whereby the air rises through the whole blood sample as bubbles. Equilibration can be achieved by bubbling air through the sample and buffer solution in the chamber for 40 seconds to equilibrate the sample to room air pO₂.

About 2 seconds after equilibration has been achieved, valve 84 is closed and valve 86 is opened to activate the positive pressure system (under about 5 psi) which causes rapid transfer (in about 0.5 second) of the equilibrated whole blood sample from the equilibration chamber 56 to the electrode sensing cuvette 58 which contains buffer solution, such as 2 ml. of pH 6.0 phosphate buffer delivered from the syringe 72. The enzyme electrode sensor then makes a rate determination of the glucose concentration.

In the presence of glucose, oxygen tension rapidly falls as oxygen is consumed at the electrode tip. The maximal rate of fall in oxygen tension is recorded and detected in less than 3 seconds. This rate is proportional to glucose concentration because of the stoichiometric relationship between oxygen and glucose that is apparent from the following equation:

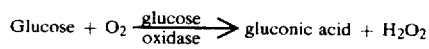
$$\text{Glucose} + O_2 \xrightarrow{\text{glucose oxidase}} \text{gluconic acid} + H_2O_2$$

Following each analysis the system is adapted automatically to wash the sample loop 26, the equilibration chamber 56 and the reaction cuvette 58 before another cycle.

In the illustrated modification, a cycle is carried out over a period of 150 seconds, making it possible to monitor the blood by separate analysis every 2½ minutes.

In operation, patient's blood is drawn in an amount to flush the heparnized solution from the tubing and to fill the loop, with the interim fluids being pumped to waste.

The apparatus is periodically standardized by opening valve 24 before or after the catheter 12 is inserted so that, upon operation of the pump 28, standard solution with a known amount of glucose can be drawn into the loop 26, after which the described normal sequence of operations are carried out to flush the calibrating solution from the loop 26 into the equilibration chamber 56 for equalization of temperature and oxygen and then from the chamber 56 into the enzyme electrode glucose sensor 60 for analysis.

The described sequence of operations of the valve, pump and syringe table can obviously be connected with suitable electrical controls for automatic sequencing of the operations on a controlled time basis for testing for blood glucose levels on repeated cycles of uniform duration whereby reliable comparisons can be made for following the course of medical procedure and/or the patient's well being.

The reliability of the test results depends somewhat on the equilibration of the blood samples and calibrating solutions for temperature and oxygen levels before the rate determination is made. Use can be made of other means for temperature and oxygen equilibration of the fluids subjected to the test. For example, instead of making use of an equilibration chamber 56 of the type illustrated in FIG. 1, use can be made of an oxygen equilibration coil of the type illustrated in the portable glucose monitor illustrated in FIG. 2 of the drawing.

Briefly described, in the illustrated portable unit, blood is drawn by pump 100 from the patient 102 through the canula 104 in an amount to fill the blood sample loop 106. The outlet from the pump 100 is connected by line 108 to a waste bag 110. A standard solution for calibrating the unit is provided in container 112 connected to a portion of the canula 104 in advance of the loop, as in the apparatus illustrated in FIG. 1, and a bag 114 of IV solution is also provided as in the apparatus illustrated in FIG. 1, for flow of IV solution to the patient while the removal of whole blood is stopped. Suitable valve members 116 and 118 are provided for controlling the flow from the calibration container and the IV bottle respectively.

A compact motorized syringe table 120 is provided for operating syringes 122, 124 and 126. The inlet to syringe 122 is connected to one end of the blood sample loop for drawing the measured amount (40 microliters) of blood from the loop plus buffer wash solution from buffer bag 132. The outlet is connected to an oxygen equilibration coil 128 of the type well known to the skilled in the art and made of a gas pervious-fluid imprevious fabric which allows oxygen from the environment to penetrate into the coil for equilibrating the oxygen concentration in the blood sample. The oxygenated blood sample is drawn by syringe 124 from the coil 128 and displaced into the receiving coil which is also formed of a fiber oxygenating tubing and from which it is flushed with additional buffer drawn from the buffer bag 132 through line 134 into the syringe 126 for displacement to the differential oxygen-glucose electrode 136 for evaluation, as previously described. The material is flushed to the waste bag 110 before a next cycle of operation is initiated.

Figure 2:
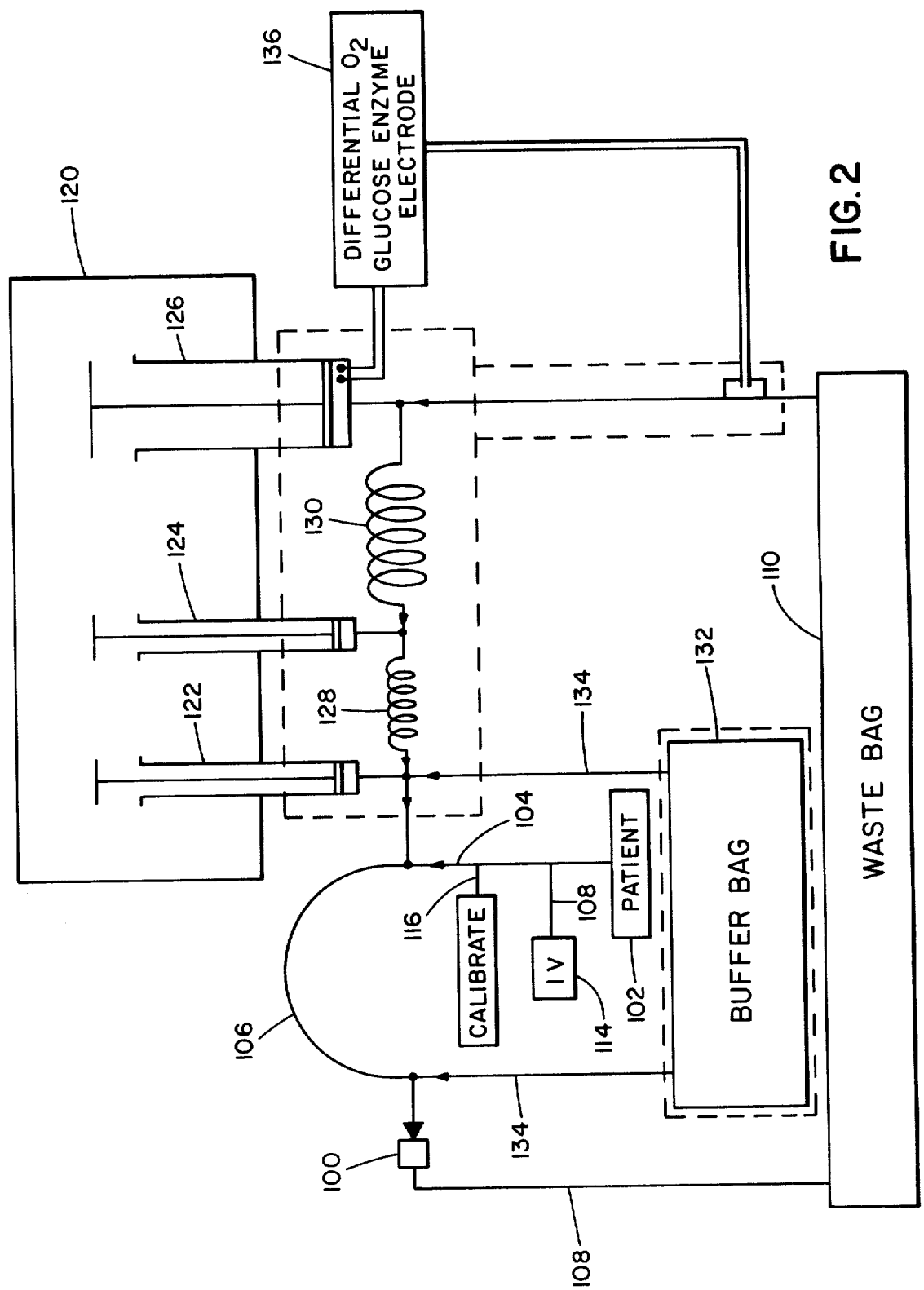
FIG. 2 is a flow diagram similar to that of FIG. 1 with modifications in the analyzer.

Temperature equilibration is effected by housing the buffer bag 132 and the coils 128 and 130 in a temperature controlled environment, such as at a temperature of 37° C., as outlined by the broken lines in FIG. 2 of the drawing.

In the modification illustrated in FIG. 2, the mixing coil 130 may be dispensed with along with syringe 124 whereby syringe 126 operates to draw the equilibrated blood sample from the coil 128 along with the additional buffer for admixture therewith before introduction into the analyzing unit.

To the present, the determination of blood (whole blood plasma or serum) has been made with a glucose oxidase enzyme reagent, as described in Clin. Chem. 14 116(1968). When glucose is added to the enzyme reagent in a stirred thermostated cell, glucose reacted with the oxygen in the presence of glucose oxidase in accordance with the reaction

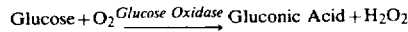

Glucose + $O_2$ $\xrightarrow{\text{Glucose Oxidase}}$ Gluconic Acid + $H_2O_2$

The amount of glucose is measured indirectly by measuring the amount of dissolved oxygen in the reaction solution.

Such technique, which makes use of glucose oxidase enzyme reagent, finds a number of objections from the standpoint of cost of the reagent and the time consumed for making a determination.

An important factor in the test procedure and apparatus described resides in the utilization of an electrode in which a small amount of glucose oxidase enzyme is immobilized on the membrane of the oxygen electrode thereby to eliminate the need for an enzyme reagent and markedly to increase the response and speed for making a determination.

An important inventive concept resides therefore in the fabrication of an electrode having a membrane of hydrophobic material, such as Teflon, a portion of which, preferably at the electrode tip, is converted to a hydrophilic surface on which the glucose oxidase enzyme can be immobilized as by a stable covalent bond.

The result is an oxygen sensor in which the only element that would penetrate the membrane is oxygen since others of the elements are either not volatile enough and/or are too polar.

Oxygen at the electrode tip is consumed in the presence of glucose oxidase. Under such circumstances, use can be made of a rate determination based upon the current output of the electrode due to the presence of glucose in the sample being tested. Under such circumstances, the electrode can exhibit some slow baseline drift while an accurate determination can be made within a few seconds. All that is required is the blood sample be diluted in a suitable buffer and equilibrated to room temperature and ambient oxygen level before the analysis is made.

Thus the blood sample is drawn from the patient and equilibrated from the standpoint of temperature and oxygen by exposing the sample to oxygen in air, as by the bubble method of the equilibration chamber 56 or by the diffusion method of the equilibration coils 128 to give the sample the oxygen tension that is ambient. Thus when initially pulled by the electrode, the electrode will read the starting oxygen tension. If glucose is present, the oxygen at the electrode tip is consumed, the effect of which is to enable a rate determination to be made from the flow of electrons based on oxygen penetration to the cathode tip of the electrode.

Briefly described, the hydrophobic electrode membrane, such as a membrane of Teflon or other hydrophobic plastic material, is etched to convert the hydrophobic surface to one that is hydrophilic. This can be accomplished, for example, with a commercial preparation of metallic sodium in naphthalene/tetrahydrofuran, such as marketed by Loctite Corporation of Newington, Connecticut. The smaller the area covered by the glucose oxidase, the more effective the analysis, since surface area is not critical when use is made of a stirred solution of the material being tested. In fact, it is sufficient if only the tip, such as a round area 25-200 microns in diameter, is treated.

For this purpose, a drop of the etchant can be placed on the membrane tip for 1 minute and then rinsed with acetone and water, followed by drying.

Next, the enzyme is mobilized as by covalent bonding the treated surface. Attachment is made with the aid of a thin layer of protein gel containing glucose oxidase enzyme. A solution of gelling protein, glucose oxidase and fixative is prepared immediately before application to the etched surface of the membrane. The following is an example of a formulation which may be used:

4 volumes of Glucose Oxidase Solution, Type VI, available from Sigma Chemical Company, St. Louis, Mo.

1 volume of 20% by weight Bovine Albumin in solution in water 1 volume of a 4% of a Paraformaldehyde solution in water A drop of the solution is placed on the etching area of the membrane, as with a plastic micropipet tip. The tip of the pipet is emptied of solution and used to remove as much solution as possible from the drop on the membrane. The remaining thin layer of solution is dried at room temperature for 1 minute and then drying is continued while the treated membrane is refrigerated at 4° C. for several hours.

The prepared glucose oxidase membrane is used in place of regular Teflon membrane in a commercial glucose analyzer instrument, such as marketed by Beckman Instrument Company of Fullerton, Calif., with no substantial alteration of the analyzer or the sample size of the plasma required for analysis. The membrane, stored at 4° C., has a shelf life of at least 8 months and its useful life will depend somewhat on the steps taken to prevent growth of microorganism.

Covalent bonding of the enzyme-gel preparation occurs by reaction with groups on the treated hydrophilic surface of the hydrophobic membrane, such as with carbonyl, hydroxyl and carboxyl groups. Instead of paraformaldehyde for immobilization and fixing of the enzyme, the enzyme can be immobilized on the membrane by the use of other bifunctional compounds having one group that attached to the etched surface and one or more other groups that provide sites for attachment of the enzyme. Representative of such other fixatives or immobilizing agent are butyraldehyde, carboxiimide, formaldehyde and other well known bifunctional coupling agents. The protein carrier gel may not be essential to the fixation of the enzyme onto the treated surface, since it can be entirely eliminated or other carriers can be employed.

EXAMPLE 1

The precision, accuracy and linearity of the automated glucose analyzer is demonstrated, using standards made up in distilled water and whole blood by addition of appropriate amounts of gravimetrically determined glucose. The aqueous standards were prepared by dissolving 10 grams of dextrose in 1 liter of distilled water. 24 hours was allowed for mutarotation. Serial dilutions were then prepared to produce 50, 100, 200, 300, 400 and 500 mg/dl standard. The whole blood samples were anti-coagulated with 200 mg ethylene diamine tetramine (EDTA) per liter of whole blood.

An anesthetized dog was used for the analysis. The analyzer was connected to the right jugular vein of the dog with a 21 gauge pediatric scalp vein needle. The left jugular vein was canulated to allow discrete blood sampling for reference glucose analyzing, and for infusion of glucose and insulin. Reference glucose determinations were made on a Beckman glucose analyzer.

Figure 3:
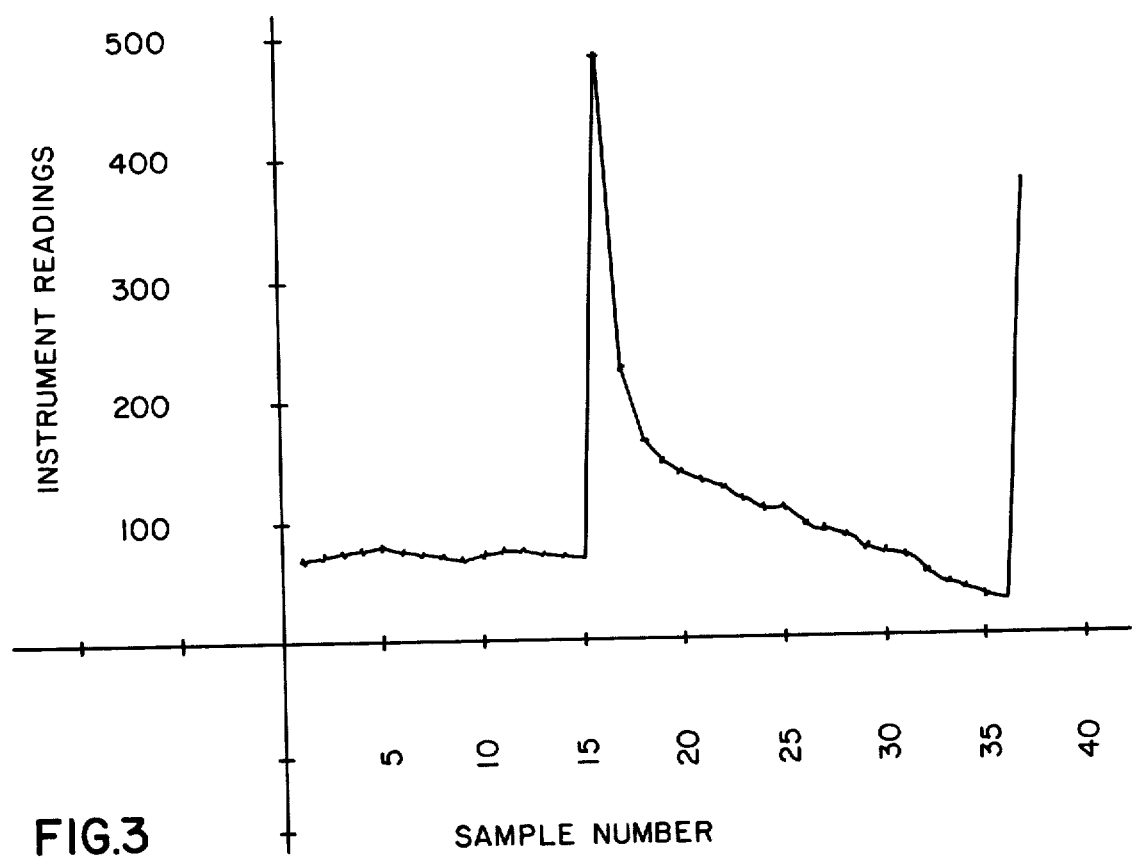
FIG. 3 is a graph of the determination for blood glucose levels derived from the example in the application.

At the start of the experiments, the automated glucose analyzer was calibrated with 100 mg/dl glucose standard. A graph representing the data from a typical experiment is presented in FIG. 3 of the drawings. As indicated in the graph, 37 minutes after the experiment started, a 16 gram glucose bolus was given intravenously. 67 minutes after the start of the experiment, 16 units of regular insulin was given intravenously. At 90 minutes after the start of the experiment, 16 grams of glucose was infused.

It will be noted from the graph that the amount of glucose detected in the blood rose precipitously each time upon infusion of glucose and that the amount of glucose in the blood was determined as having fallen to lower levels in response to the infusion of insulin.

With daily use of the instrument described, sufficient enzyme activity remained immobilized on the membrane having the electrode so that it was necessary to change the membrane only after two to four weeks, providing the membrane surface contact and antibacterial solution such as a solution of benzoic acid in 0.2 M phosphate buffer at pH 7.4. If the same enzyme membrane is used briefly daily and stored at 4° C. when not in use, loss of enzyme activity over a one month period will be found to be less than 5%.

Figure 4:
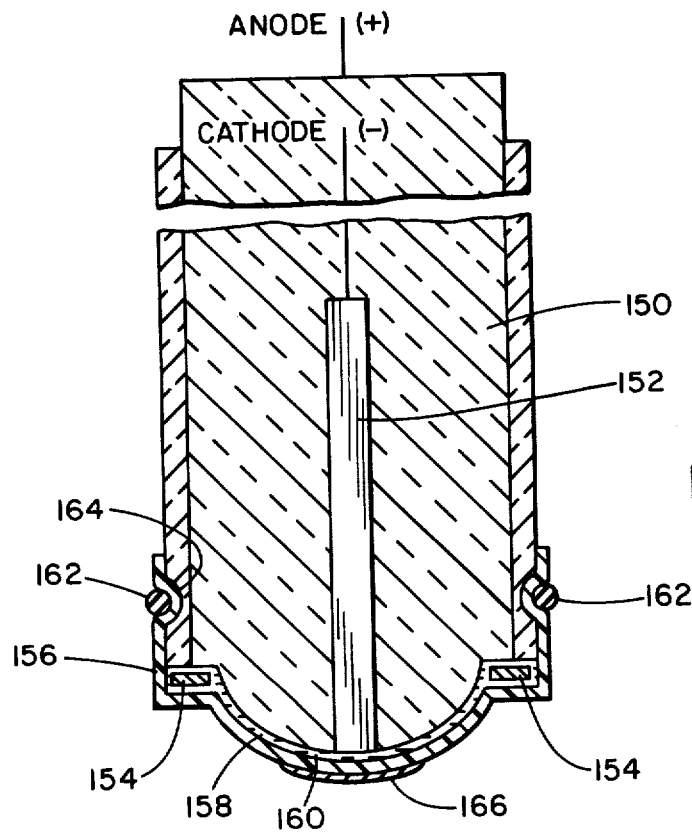
FIG. 4 is a schematic sectional elevational view of an electrode embodying the features of this invention.

The electrode employed in the practice of this invention, with the enzyme immobilized on the surface of the membrane, is illustrated in FIG. 4 wherein the base of the electrode comprises a glass rod 150 having a cathode in the form of a platinum electrode 152 which extends to the tip of the rod 150, and anodes in the form of silver chloride reference electrodes 154 which extend into the space between the end portion of the glass rod and a Teflon membrane 156 that is secured onto the end of the electrode with a space 158 in between that is filled with electrolyte 160. The membrane of Teflon is releasably mounted onto the end portion of the glass rod by means of an O-ring 162 which seats in an annular groove 164 of the rod sealably to engage portions of the membrane 156 which span the groove. The enzyme is immobilized on the gel layer 166 bonded, as heretofore described, on the outer surface of the membrane layer, at the tip portion of the electrode. The electrode is similar in construction to that described in U.S. Pat. No. 3,542,662 except for the membrane with the enzyme immobilized in a layer bonded to the outer surface of the membrane at the tip of the electrode.

As previously described, the blood glucose analyzer of this invention is based on a polargraphic detection system in which the specificity for oxygen is excellent since oxygen is the only electro-active substance in blood defusible through a Teflon membrane for reaction at the electrode. The specificity of glucose oxidase for glucose has also been established. By operation of the glucose sensor in a rate determination mode, any base line drift in the oxygen electrode is eliminated.

There are a number of distinct advantages to the invention described and claimed, namely: the blood sampling can be carried out on frequent intervals, such as 150 seconds. This minimizes the amount of blood removed from the patient for analysis and facilitates the maintenance of a clot-free sampling system by comparison with continuous sampling. The amount of heparin infused into the patient between sampling cycles is not sufficient to cause any significant degree of systematic heparnization. By avoiding infusion of the sample blood back into the patient, the chance of sepis is greatly reduced. The use of an immobilized enzyme electrode in the glucose detector permits miniaturization and simplification of operation with minimal reagent requirement. Within seconds after sampling, the result can be secured for the glucose concentration in the patient's blood.

It will be apparent from the foregoing that a significant improvement is provided in a system for blood glucose analysis and in elements employed in analysis equipment whereby rapid and accurate determinations of blood glucose can be made on site for monitoring glucose levels in a patient's blood.

It will be understood that changes may be made in the details of construction, arrangement and operation, without departing from the spirit of the invention, especially as defined in the following claims.

I claim:

1. A method for monitoring blood glucose levels consisting essentially of the steps of withdrawing patient's whole blood, uniformly oxygenating increments of the patient's withdrawn blood by contacting the increment of withdrawn patient's blood with air for a sufficient length of time to effect oxygen equilibration, transferring the increment of blood after air-oxygen equilibration to a sensor having an electrode covered with a hydrophobic membrane having an etched hydrophilic surface on which glucose oxidase is immobilized whereby oxygen is consumed by reaction with glucose in the blood in the presence of the glucose oxidase, measuring rate of change in oxygen tension resulting from the reaction of glucose in the blood, said rate of change being proportional to the glucose concentration in the blood, and diluting the increment of patient's blood before measuring for rate of change in oxygen tension.

2. The method as claimed in claim 1 in which determinations are made on an intermittent basis at frequent intervals continuously to monitor the blood glucose level of the patient.

3. The method as claimed in claim 1 in which a catheter for the withdrawal of the patient's blood remains inserted in the blood vessel of the patient for withdrawal of blood at frequent intervals for continuous monitoring of the patient's blood glucose level.

4. The method as claimed in claim 3 which includes the step of flowing an IV solution to the catheter during the period of time between blood withdrawal.

5. The method as claimed in claim 4 in which the IV solution contains an anti-coagulant in an amount sufficient to insure the absence of clotting in the blood sampling system but insufficient to cause a significant effect on the coagulating ability of the patient's blood.

6. The method as claimed in claim 5 in which the anti-coagulant is heparin.

7. The method as claimed in claim 1 which includes the step of removing the increment of blood from the sensor and flushing the sensor with buffer solution in preparation for the introduction of a next increment of equilibrated patient's blood for testing.

8. The method as claimed in claim 1 which includes the step of equilibrating the increment of the patient's blood as to temperature as well as to oxygen levels before measurement of oxygen consumption.

9. The method as claimed in claim 8 in which the increment of blood is equilibrated to a temperature of about 37° C.

10. The method as claimed in claim 1 in which the increment of blood is equilibrated for oxygen level by bubbling the air through the increment for a period of time.

11. The method as claimed in claim 1 in which the increment of blood is equilibrated for oxygen level by holding the blood in an oxygen equilibration coil exposed to atmospheric air for diffusion of oxygen therethrough from the atmosphere to the blood.

12. The method as claimed in claim 1 in which the sensor operates in a rate determination mode based upon the rate of oxygen consumption by the glucose present in the blood at the electrode.

13. The method as claimed in claim 1 which includes the step of mixing the increment of blood with a buffer solution before the equilibration step.

14. The method as claimed in claim 13 in which the increment of blood is flushed to the sensor with the buffer.

15. The method as claimed in claim 1 in which the steps are automated for operation in sequence to withdraw the blood and flush the sensor with the buffer, to drain an IV solution to the catheter during the period of time that blood is not being withdrawn and flushing the increment of blood with buffer for equilibration, equilibrating the oxygen level and temperature of the flushed increment of blood, flowing the equilibrated blood into the sensor for a rate determination of the glucose level in the blood, and flushing the blood from the sensor to waste.

16. The method as claimed in claim 1 in which the hydrophobic membrane is polytetrafluoroethylene (Teflon) having an etched hydrophilic surface on which the glucose oxidase is immobilized.

* * * * *